United States Patent [19]

Jacobs

[11] Patent Number: 4,719,085
[45] Date of Patent: Jan. 12, 1988

[54] MOUNT FOR AMMONIA-SENSITIVE TEST ELEMENTS

[75] Inventor: Merritt N. Jacobs, Fairport, N.Y.

[73] Assignee: Eastman Kodak Company, Rochester, N.Y.

[21] Appl. No.: 813,218

[22] Filed: Dec. 24, 1985

[51] Int. Cl.[4] .................... G01N 31/22; G01N 33/50; C12Q 1/58

[52] U.S. Cl. .................................... 422/56; 422/57; 422/58; 422/104; 435/12; 435/805; 436/113; 436/165

[58] Field of Search ............... 422/56, 57, 58, 102, 422/104; 436/165, 113; 435/12, 805

[56] References Cited

U.S. PATENT DOCUMENTS

| | | | |
|---|---|---|---|
| 4,223,089 | 9/1980 | Rothe et al. | 436/113 |
| 4,298,345 | 11/1981 | Sodickson et al. | 422/56 X |
| 4,440,301 | 4/1984 | Intengan | 422/57 X |
| 4,564,503 | 1/1986 | Greisch | 422/58 X |

Primary Examiner—Barry S. Richman
Assistant Examiner—Jill Johnston
Attorney, Agent, or Firm—Dana M. Schmidt

[57] ABSTRACT

There is described a dry chemistry test element consisting of a chemistry unit and a mount that is ammonia-sensitive, wherein the mount is improved to prevent ammonia carry-over from test element to test element. The improvement is based upon the discovery that in previous test elements which were joined together using ultrasonic bonding along energy-directing ribs, ammonia carry-over was created by the leakage of ammonia from one ammonia-sensitive element to another test element. Each element had a construction of a mount that provided a gas leakage path into the viewing aperture of the bottom sheet of the mount. The elements of the invention are provided with a smooth area on the bottom sheet which is fixed to the chemistry unit with an adhesive while the rest of the mount is joined at the energy-directing ribs.

2 Claims, 2 Drawing Figures

MOUNT FOR AMMONIA-SENSITIVE TEST ELEMENTS

FIELD OF THE INVENTION

This invention relates to test elements for use in assaying for analytes in liquids, particularly such elements that are ammonia-sensitive.

BACKGROUND OF THE INVENTION

In the clinical analysis of blood, one of the more important and frequently performed tests that are run is the one for blood urea nitrogen (BUN). BUN is tested to determine, e.g., abnormal kidney behavior. Conventionally, such a test relies upon the conversion of the urea into ammonia gas, and the reaction of a leuco dye and the gas to form a dye, the density of which is proportional to the amount of urea present.

A recent improvement in the BUN tests is the use of dry chemistry test elements to conduct the test. As used herein, "dry chemistry" refers to the absence of liquid reagents, characteristic of wet assays, in the element or analyzer used with the elements, prior to use. Instead, all the reagents appear in a test element in one or more reagent layers, which are dry to the touch. A representative patent describing preferred dry chemistry BUN test elements is U.S. Pat. No. Re. 30,267 by Bruschi.

Although BUN test elements constructed in the manner described by the aforesaid patent have enjoyed great commercial acceptance, there remained prior to this invention a minor problem called "ammonia carryover." There are other dry chemistry test elements that measure ammonia gas, but in much smaller quantities. For example, a creatinine test element (also used to test for kidney malfunctions) uses creatinine iminohydrolase to convert the creatinine into ammonia gas, which is measured using a leuco dye having a higher coefficient of extinction than the one used in the Bun test element. Because it is inevitable that some ammonia gas will escape from the aforesaid BUN test element during use, if a creatinine test element is close by such a BUN test element during use, ammonia "carries over" into the creatinine element. There is a further aspect of the creatinine assay which exacerbates the problem. An ammonia blank measurement is made on the serum to subtract out the serum ammonia present, which is otherwise an interferant. The ammonia blank element also measures ammonia, as is readily apparent. Since both the creatinine element and the ammonia element blank are designed to be 10,000 times as sensitive to such gas as is the BUN element, any such carry-over presents a serious problem. The problem is particularly acute in analyzers, such as those described in U.S. Pat. No. 4,303,611, wherein the dry chemistry test elements are incubated in a stack each one next to and in contact with another.

This problem was known prior to this invention, but what was not known was its exact cause. Many attempts have been made to deal with this ammonia carry-over problem. For example, one possibility is to instruct the user to avoid testing the creatinine element in close proximity with a BUN element. Or alternatively, evaporation caps can be provided to attempt to keep ammonia from escaping from BUN elements. Also, vent holes were formed in the supports of the test elements, and non-absorbing surfaces have been provided in the analyzer.

None of those attempts have been very successful, particularly when the test elements are stacked as noted above. For example, venting the incubator support to allow released gas to escape to the atmosphere leaves unsolved the problem that the released gas will not be available to the indicator, thereby producing a reduction in sensitivity. Furthermore, warning the user to be careful about "close proximity" is not satisfactory, compared to finding a safeguard that can be built into either the test chemistry or the analyzer. No such satisfactory built-in safeguard had been found prior to this invention, particularly for analyzers that stack incubating elements. Even non-stacking analyzers would benefit from sensitivity improvement.

SUMMARY OF THE INVENTION

I have discovered that the cause of the problem resides in the manner of construction of the mount of the test elements that holds the chemistry unit. Such mount, as heretofore constructed, provides a ready leakage path of the gas to the chemistry unit. The solution to the problem, which follows from this discovery of the cause, is an improved design of the test element.

More specifically, there is provided a test element comprising a generally planar chemistry unit that is ammonia-sensitive, and a plastic mount surrounding and supporting the chemistry uint, the chemistry unit comprising a transparent, non-abosrbent layer onto which the ammonia-sensitive reagents of the chemistry unit are disposed in one or more layers, and the mount comprising a base sheet and a cover sheet with the chemistry unit sandwiched between the sheets, and means for securing the base sheet, chemistry unit, and cover sheet into an integral test element. The base sheet includes a viewing aperture generally centered therein, and the cover sheet includes a dispensing aperture generally centered therein. The test element is improved in that the surface of the base sheet in contact with the chemistry unit is relatively smooth to provide a uniform contact area with the chemistry unit, and in that adhesive is disposed between the base sheet and the chemistry unit at the contact area, whereby any ammonia gas leakage into the test element from an adjacent test element via the viewing aperture is stopped at the contact area.

Accordingly, it is an advantageous feature of this invention that an ammonia-sensitive test element is provided that inherently guards against ammonia carry-over from a test element underneath the base sheet that generates ammonia.

It is a related advantageous feature of the invention that such a test element can be used on top of other dry chemistry test elements without regard to whether any of them is a BUN element, or one which is designed to generate ammonia gas.

Another related advantageous feature of the invention is that test elements constructed in accordance with the invention cannot become ammonia sinks that draw the ammonia gas out of adjacent elements, e.g., the creatinine element so as to cause a negative bias.

Other advantageous features will become apparent from the detailed discussion of the preferred embodiments, when read in light of the attached drawings.

DESCRIPTION OF THE PREFERRED EMBODIMENTS

Figure 1:
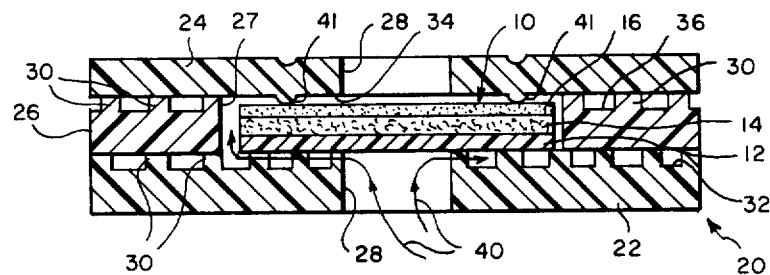
FIG. 1 is a section view of a dry chemistry test element constructed in accordance with the prior art.

The description which follows is directed to the preferred embodiment of a dry chemistry test element constructed for the analysis of creatinine in blood serum, and particularly, such elements that are used in an analyzer that stacks the test elements together. In addition, it is applicable to any test element that is ammonia-sensitive, for example the BUN or blood ammonia test elements, regardless of whether the test liquid is serum or some other biological liquid such as urine or whole blood, or industrial liquid, or is used in an analyzer having a stacking incubator or one without.

The creatinine test elements of both the prior art and of this invention comprise a chemistry unit, and a mount for the chemistry unit. The chemistry unit, shown as 10 in FIG. 1, remains the same in both cases, and generally comprises the test element described in U.S. Pat. No. 4,276,377, issued on June 30, 1981. Such a unit comprises a transparent, nonabsorbent layer 12 such as polyethylene terephthalate, on which are deposited one or more layers 14 and 16 containing the necessary reagents for the reaction. Additionally, one or more layers (not shown) providing a liquid spreading function, or the blockage of liquid interferants, preferably are included.

The mount 20 constructed in accordance with the prior art is described in U.S. Pat. No. 4,230,757. Preferably, such a mount comprises a base sheet 22, a cover sheet 24, and a spacer frame 26 having an aperture 27. Each of the cover and base sheets has an aperture 28 generally centered therein, the aperture of the base sheet being a viewing aperture, and the aperture of sheet 24 being the liquid access aperture for the dispensing of sample liquid onto the element. Sheets 22 and 24 and frame 26 are assembled with chemistry unit 10 sandwiched between layers 22 and 24, and within the aperture 27 of frame 26.

The bonding of the sheets together is achieved by ultrasonically welding sheet 22 to frame 26, and frame 26 to sheet 24. That is, all of sheets 22, 24 and frame 26 comprise a thermoplastic such as polystyrene, which will bond when ultrasonically heated. To assist in such bonding, energy-directing ribs 30 are provided in surface 32 of sheet 22 facing the chemistry unit 10 and frame 26, and in surface 36 of frame 26 facing the sheet 24. The inner surface 34 of sheet 24 that faces frame 26 is relatively smooth. These ribs then weld the sheets and frame 26 together. Some welding also may occur between sheet 22 and layer 12. Additionally, dimples 41 optionally are included to function as stakes that prevent the chemistry unit 10 from moving around in aperture 27.

In accord with one aspect of the invention, I have discovered that the cause of ammonia carry-over into such an element is the presence of ribs 30 in sheet 22. Such ribs do not adequately bond to layer 12 in such a way as to create an air-tight seal. Instead, ammonia gas flows, arrows 40, between layer 12 and the ribs, and up into the aperture 27 in which chemistry unit 10 is confined. It is at this point the ammonia gas contaminates the chemistry unit.

Figure 2:
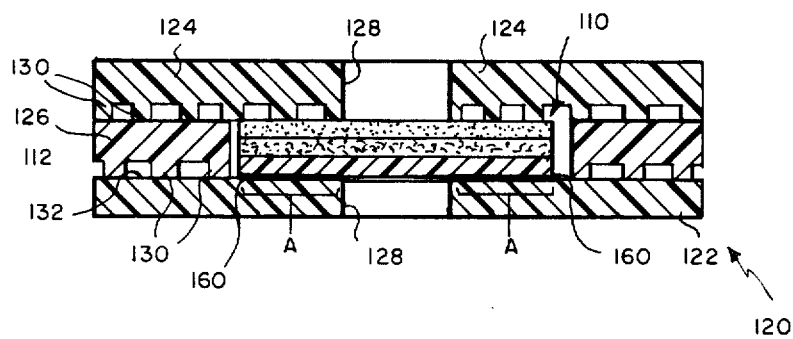
FIG. 2 is a section view similar to that of FIG. 1, except that the invention is illustrated.

The solution to the problem comprises a reversal of the positions of sheets 22 and 24, so that the cover sheet of the prior art becomes the base sheet of the invention. More importantly, the base sheet is provided, FIG. 2, with a smooth inner surface, as follows: (Parts similar to those previously described are given the same reference numeral to which a 100 is appended.)

The mount 120 that confines and supports chemistry unit 110 (which is identical to unit 10), comprises base sheet 122, cover sheet 124, and frame 126. Both sheets 122 and 124 are apertured at 128. However, unlike the prior art, surface 132 of sheet 122 is essentially smooth throughout, especially in the area of contact A with non-absorbent layer 112 of chemistry unit 110, which is an annular ring if unit 110 is circular.

To avoid having to construct new parts for the manufacture of such mount 120, the old parts for prior art mount 20 are utilized as follows: cover sheet 24 becomes base sheet 122, base sheet 22 becomes cover sheet 124 but with ribs 130 projecting downwardly, and frame 126 is frame 26 except turned over with ribs 130 facing base sheet 122 rather than the cover sheet.

Further in accordance with the invention, an adhesive 160 is applied to contact area A, to bond sheet 122 to layer 112 throughout all of contact area A, thus encircling viewing aperture 128. This then precludes any gas contamination from passing to unit 110 via aperture 128 of sheet 122. Any ammonia-free adhesive will suffice that sets upon standing over a temperature range of $-20°$ F. to $100°$ F., for example, a polyester adhesive such as a polyester of 1,3-cyclohexane dicarboxylic acid and diethylene glycol-neopentyl glycol (50:50).

Alternatively, other bonding methods, such as adhesive, can be used to bond sheets 122 and 124 and frame 126 together, so that ribs 130 can be eliminated. Also, ribs 130 can be placed solely in the opposite surfaces of frame 126. However, even in such alternative constructions, gas leakage can still occur through aperture 128 of cover sheet 124. To avoid this, all the ammonia-sensitive elements which necessarily generate ammonia, and are used together in the analyzer, are preferably constructed as described above. In this manner, if a BUN test element is stacked above a creatinine element, any gas generated in the upper, BUN element will not be able to leak out the base sheet down into the creatinine element below it. This is even useful if two serum ammonia test elements are stacked together. One of these may release more ammonia than the other one. Whether the element containing the greater-amount ammonia is above or below the lesser-amount-containing element, it still will not contaminate the lesser-amount-containing element if both elements are constructed as per this invention.

Yet another advantage of this invention is that, by reason of the adhesive bonding that occurs in contact area A, the dimples 41, FIG. 1, can be elminated.

The invention has been described in detail with particular reference to preferred embodiments thereof, but it will be understood that variations and modifications can be effected within the spirit and scope of the invention.

What is claimed is:

1. In a test element comprising a generally planar chemistry unit that is ammonia-sensitive, and a plastic mount surrounding and supporting said chemistry unit, said chemistry unit comprising a transparent, non-absorbent layer and at least one layer in which ammonia-sensitive reagents are disposed, said mount comprising a base sheet and a cover sheet assembled with said chemistry unit sandwiched between said sheets, said base sheet including a viewing aperture generally centered therein, and said cover sheet including a dispensing aperture generally centered therein, and means for securing said base sheet, said chemistry unit, and said cover sheet into an integral test element, said means for securing comprising ultrasonic energy-directing ribs on one of said base sheet and said cover sheet for bonding said base sheet to said cover sheet;

the improvement wherein the surface of said base sheet in contact with said chemistry unit is essentially smooth to provide a uniform contact area with said chemistry unit, said chemistry unit is disposed within said mount with said transparent layer being adjacent said smooth base sheet surface, and wherein an adhesive is positioned under said transparent layer and disposed between said base sheet and said chemistry unit at said contact area and encircling said viewing aperture, whereby any ammonia gas leakage into said test element from an adjacnet test element via said viewing aperture is stopped at said contact area.

2. An element as defined in claim 1, further including a frame sandwiched between said base and cover sheets, said frame being apertured to accommodate said chemistry unit inside of said frame, said frame being bonded to said base sheet and said cover sheet through ultrasonic energy directing ribs located solely in a surface of said frame and said cover sheet.

* * * * *

UNITED STATES PATENT AND TRADEMARK OFFICE
CERTIFICATE OF CORRECTION

PATENT NO. : 4,719,085
DATED : January 12, 1988
INVENTOR(S) : Merritt N. Jacobs

It is certified that error appears in the above-identified patent and that said Letters Patent are hereby corrected as shown below:

Column 4, line 27, "glycol-neopentyl" should read --glycol/neopentyl--.

Column 6, line 2, "aperture," should read --aperture;--.

Column 6, line 4, "adjacnet" should read --adjacent--.

Signed and Sealed this

Fourteenth Day of June, 1988

Attest:

DONALD J. QUIGG

Attesting Officer

Commissioner of Patents and Trademarks